(12) United States Patent
Hasan et al.

(10) Patent No.: US 6,200,793 B1
(45) Date of Patent: Mar. 13, 2001

(54) COLD-ACTIVE PROTEASE CP70

(75) Inventors: A. K. M. Quamrul Hasan, Kobe; Eiichi Tamiya, Tatsunokuchi-machi, both of (JP)

(73) Assignees: The Procter & Gamble Company, Cincinnati, OH (US); Japan Advanced Institute of Science and Technology, Hokuriku (JP)

( * ) Notice: Subject to any disclaimer, the term of this patent is extended or adjusted under 35 U.S.C. 154(b) by 0 days.

(21) Appl. No.: 09/117,245

(22) PCT Filed: Jan. 24, 1997

(86) PCT No.: PCT/US97/01148

§ 371 Date: Jul. 27, 1998

§ 102(e) Date: Jul. 27, 1998

(87) PCT Pub. No.: WO97/27313

PCT Pub. Date: Jul. 31, 1997

(30) Foreign Application Priority Data

Jan. 26, 1996 (JP) .................................................. H8-12207

(51) Int. Cl.[7] ............................... C12N 9/52; C12N 9/50; C12N 1/00; A61K 38/00; A23J 1/00
(52) U.S. Cl. ........................ 435/220; 435/219; 435/850; 530/300; 530/412
(58) Field of Search .................................... 435/220, 219, 435/850; 530/300, 412

(56) References Cited

U.S. PATENT DOCUMENTS 4,778,878 * 10/1988 Adams et al. ....................... 530/328
5,646,028 * 7/1997 Leigh .................................. 435/220

OTHER PUBLICATIONS

Kato et al., "Protease Formation by a Marine Psychrophilic Bacterium.": Agr. Biol. Chem., vol. 36, No. 7, p. 1177–1184, 1972.

Shikata et al., "Detection of Large COOH–Terminal Domains Processed from the Precursor of *Serratia marcescens* Serine Protease in teh Outer Membrane of *Escherichia coli*", *J. Biochem 111*, 627–632 (1992).

Kato et al., "Purification and Properties of Proteases from a Marine–psychrophilic Bacterium", Agr. Biol. Chem., vol., No. 7 p. 1183–1192 (1972).

* cited by examiner

*Primary Examiner*—Tekchand Saidha
(74) *Attorney, Agent, or Firm*—Kevin L. Waugh; C. Brant Cook; Kim William Zerby (57) ABSTRACT

A psychrophilic protease is here disclosed which has the following physicochemical properties: (a) specific activity and substrate specificity: the protease acts on casein, gelatin, hemoglobin and albumin to specifically decompose them, and the substrate specificity decreases in the order of casein, gelatin, hemoglobin and albumin; (b) optimal pH: 8.0; (c) pH stability: the protease is stable in the range of pH 6.5 to pH 10.0 at 30° C. for 1 hour; (d) optimal temperature: about 40° C.; (e) temperature stability: at pH 7 for 1 hour, the protease is active at a temperature up to 30° C., but it is inactivated at 40° C. as much as about 40% and completely inactivated at 50° C. in about 10 minutes; (f) enzyme activity: the protease has 50% or more of its maximum activity at about 20° C.; (g) the active center of the enzyme is serine; and (h) the molecular weight of the protease is about 70 kDa as measured by SDS-PAGE.

1 Claim, 6 Drawing Sheets

COLD-ACTIVE PROTEASE CP70

This is a 371 of PCT/US97/01148 filed Jan. 24, 1997, which claims priority to JP H8-12207 filed January 26, 1996, which is pending.

BACKGROUND OF THE INVENTION (i) Field of the Invention

The present invention relates to a protease having a high activity at a low temperature and its utilization.

(ii) Description of the Related Art

Psychrophilic bacteria have been known for a long time, and their existence can be confirmed extensively in low temperature circumstances. For example, psychrophilic bacteria can be isolated from soils, fishery products, milk products as well as artificial low temperature circumstances. Researches on psychrophilic bacteria have been conducted in accordance with food microbiological requirements, but they have principally been confined to those with respect to the phylogeny of microorganisms.

Enzymes obtained from psychrophilic bacteria are expected to be cold-active is enzymes having an optimal temperature in a low temperature range. The cold-active enzyme which acts efficiently at the low temperature is considered to be capable of being incorporated into, for example, a detergent which can be used even in water at the low temperature. It is also considered to be employed for a chemical reaction in the presence of an organic solvent which is volatile at ordinary temperature and for the quality improvement of foods at the low temperature at which the foods do not rot. Furthermore, the investigation on the enzyme derived from the psychrophilic bacteria is fairly interesting to reveal the physiological functions and the adaptation mechanism to the low temperature of the psychrophilic bacteria.

SUMMARY OF THE INVENTION

The present inventors have now found that a protease can be isolated from the supernatant liquid of a culture medium of a *Flavobacterium balustinum* P104 strain and then purified, and that the isolated and purified protease has activity at a low temperature. The present invention is based on such knowledge.

Therefore, an object of the present invention is to provide a cold-active protease.

Another object of the present invention is to provide a method for preparing the above-mentioned cold-active protease by the use of a *Flavobacterium balustinum* P104 strain.

Still another object of the present invention is to provide a peptide comprising an amino acid sequence present at the N terminal of the cold-active protease.

The protease according to the present invention has a part or all of the following physicochemical properties.

Specific activity and substrate specificity: The protease acts on casein, gelatin, hemoglobin and albumin to specifically decompose them in the order of casein, gelatin, hemoglobin and albumin.

Optimal pH: 8.0 pH stability: The protease is stable in the range of pH 6.5 to pH 10.0 at 30° C. for 1 hour.

The protease according to the present invention further has a part or all of the following physicochemical properties.

Optimal temperature: About 40° C.

Temperature stability: At pH 7 for 1 hour, the protease is scarcely inactivated at a temperature up to 30° C., but it is inactivated at 40° C. as much as about 40% and completely inactivated at 50° C. in about 10 minutes.

Enzyme activity: The protease has about 50% or more of its maximum activity at 20° C.

The active center of the enzyme is serine.

The molecular weight of the protease is about 70 kDa as measured by SDS-PAGE.

Furthermore, the protease according to the present invention consists of a protein containing a part or all of an amino acid sequence described in SEQ ID NO:1, or a protein containing a part or all of an amino acid sequence described in SEQ ID NO:1 at its N terminal.

According to another aspect of the present invention, we provide a protease having about 50% or more of its maximum activity at 20° C.

According to still other aspects of the present invention, we provide a protease which consists of a protein containing a part or all of an amino acid sequence described in SEQ ID NO:1, and a protease which consists of a protein containing a part or all of an amino acid sequence described in SEQ ID NO: 1 at its N terminal.

A method for preparing the above-mentioned protease according to the present invention comprises the steps of culturing *Flavobacterium balustinum* P104 (FERM BP-5006) for producing tprotease, and then collecting the protease from its culture medium.

DETAILED DESCRIPTION OF THE INVENTION

Characteristics of Enzyme

The characteristics of an enzyme according to the present invention are as follows.

(1) Specific Activity and Substrate Specificity

The enzyme according to the present invention acts on casein, gelatin, hemoglobin and albumin to specifically decompose them. The substrate specificity of the enzyme decreases in the order of casein, gelatin, hemoglobin and albumin.

(2) Optimal pH

The optimal pH of the enzyme according to the present invention is 8.0. Furthermore, the enzyme retains about 90% or more of a maximum activity in the range of pH 6.5 to pH 9.5.

(3) pH Stability

The enzyme according to the present invention is stable at 30° C. for 1 hour in the range of pH 6.5 to pH 10.0.

(4) Optimal temperature

The optimal temperature of the enzyme according to the present invention is 40° C. at pH 10 and pH 7. At a temperature of 30° C., the enzyme retains about 80% of the maximum activity at pH 10 and about 90% of the maximum activity at pH 7. At a temperature of 50° C., the enzyme retains about 10% of the maximum activity at pH 10 and about 80% of the maximum activity at pH 7.

With regard to savinase which is a commercially available enzyme, its optimal temperature is 60° C. In addition, with regard to most of known psychrophilic enzymes, their optimal temperatures are about 40° C. Therefore, the enzyme according to the present invention can be considered to be a psychrophilic enzyme.

(5) Temperature Stability

At pH 7 for 1 hour, the enzyme according to the present invention is scarcely inactivated at a temperature up to 30° C., but it is inactivated at 40° C. as much as about 40% and completely inactivated at 50° C. in about 10 minutes. Therefore, the enzyme according to the present invention can be considered to be a psychrophilic enzyme.

(6) Enzyme Activity

The enzyme according to the present invention has about 50% or more of its maximum activity at 20° C.

In consequence, according to another aspect of the present invention, we provide a protease having about 50% or more of its maximum activity at 20° C.

(7) Inhibition of Activity

The protease activity of the enzyme according to the present invention is not inhibited by any of pepstatin, L-trans-epoxysuccinylleucylaido4-guanidinobutane (E-64), iodoacetamide and 1,10-phenanthroline, but it is notably inhibited by phenylmethanesulfonyl fluoride (PMSF) and ethylenediaminetetraacetic acid (EDTA). In view of this fact, it can be suggested that the enzyme according to the present invention is a serine protease. Therefore, the active center of the enzyme according to the present invention can be considered to be serine.

(8) Molecular Weight

The enzyme according to the present invention has a molecular weight of about 70 kDa as measured by SDS-PAGE.

(9) Amino Acid Sequence at N Terminal

The amino acid sequence at the N tenninal of the enzyme according to the present invention is described in SEQ ID NO:1. With regard to the amino acid sequence at the N terminal of the enzyme according to the present invention, its homology with each amino acid sequence of known proteins was inspected by the use of a data bank "Entrez", and as a result, it was apparent that the amino acid sequence at the N tenninal had no homology with any amino acid sequences of the known proteins. Accordingly, the protease according to the present invention may consists of a protein containing a part or all of an amino acid sequence described in SEQ ID NO:1 or a protein containing a part or all of an amino acid sequence described in SEQ ID NO:1 at its N terminal.

Furthermore, according to still other aspects of the present invention, we provide a protease consisting of a protein containing a part or all of an amino acid sequence described in SEQ ID NO:1, and a protease consisting of a protein containing a part or all of an amino acid sequence described in SEQ ED NO:1 at its N terminal. This protease may have such characteristics as described in the above-mentioned (1) to (8).

Here, "the protein containing a part or all of an amino acid sequence described in SEQ ID NO:1" includes a protein in which an optional amino acid sequence is added to an N terminal and/or a C terminal of a part or all of the amino acid sequence described in SEQ ID NO:1.

Preparation Method of Protease

A protease according to the present invention can be produced by the use of microorganisms. The production microorganisms belong to a Flavobacterium genus, and any microorganisms are usable, so far as they have an ability for producing the protease.

A preferable example of the microorganisms having the ability for producing the protease according to the present invention is a *Flavobacterium balustinum* P104 strain. This strain is microorganisms separated from the intestine of salmon by the present inventors, and they are deposited in Agency of Industrial Science and Technology, Biotechnology Research Institute under Deposition No. FERM BP-5006 on Feb. 17, 1995.

In culturing the strain which can be used in the present invention, a culture medium may be liquid or solid, but a shake culture or an aeration spinner culture using a liquid culture medium is usually used.

As the culture medium for culturing the microorganisms therein, any medium is usable, so far as it can produce the protease. That is to say, as a carbon source, there can be used, for example, glucose, trehalose, fructose, maltose, sucrose, starch and malt oligo-saccharide. As a nitrogen source, there can be used, for example, peptone, yeast extract, malt extract, meat extract, soybean powder, cotton seed powder, cone steep liquor, various amino acids and their salts, and nitrates. A synthetic medium or a natural medium which can be used in the present invention suitably contains the above-mentioned carbon source and nitrogen source, inorganic salts such as magnesium phosphate, calcium, sodium, potassium, iron and manganese as well as other nutrients, as needed.

Culturing conditions such as the pH and the culture temperature of the culture medium can be suitably altered, so far as they permit the production of the protease, but in the case of the shake culture or the aeration spinner culture, it is preferred that the pH is about neutral and the culture temperature is from 10° C. to 20° C.

The protease of the present invention is present in cell walls of bacteria, cells of the bacteria and the supernatant of a culture medium, and it may be used in any form such as bacterial cells, a crude enzyme obtained from the bacterial cells or the supernatant of the culture medium, or an extracted and purified enzyme. Alternatively, the protease immobilized by a known method can also be used.

In order to collect and purify the protease of the present invention from the culture medium, known purification methods can be utilized singly or in combination thereof.

Since the protease according to the present invention is mainly excreted extracellularly, namely into the culture medium, a crude enzyme solution can easily be obtained by removing the bacterial cells with the aid of filtration or centrifugation. This crude enzyme can be further purified by a known purification method. Examples of the known preferable purification method include a salting-out method using a salt such as ammonium sulfate, a precipitation method using an organic solvent (e.g., methanol, ethanol or acetone), an adsorption method using raw starch, an ultrafiltration method, and various chromatographical methods such as gel filtration chromatography and ion exchange chromatography. Typical embodiments of the preferable purification methods will be described in the undermentioned examples.

Utilization of Enzyme

The psychrophilic protease according to the present invention has an optimal temperature in a low temperature range. Thus, the psychrophilic protease of the present invention permits the decomposition reaction of a protein to be carried out in low temperature environments. For example, a detergent utilizable even in low temperature water can be prepared by adding the protease according to the present invention to a detergent composition for clothes. This detergent composition can be prepared in accordance with a conventional method except that the psychrophilic protease according to the present invention is added. That is to say, the detergent can be formed by blending the protease of the present invention with ordinary detergent components such as a surface active agent for the detergent, a bleach, a builder and the like.

Furthermore, the psychrophilic protease according to the present invention enables the reaction to proceed at a low temperature. Therefore, even if an organic solvent which is volatile at ordinary temperature is present in the reaction system, the reaction can be carried out at a low temperature at which the organic solvent component is not volatilized. Moreover, when it is attempted to improve the quality of a food by the use of the protease according to the present invention, the reaction proceeds advantageously at a low temperature, whereby the food can be effectively prevented from rotting. In addition, since the protease according to the present invention is provided, it can be expected to advance the elucidation of the physiological mechanism of psychrophilic bacteria and their application mechanism to a low temperature.

Protein having Amino Acid Sequence at N Terminal

According to another aspect of the present invention, we provide a peptide consisting of a part or all of an amino acid sequence described in SEQ ID NO:1, a protein comprising a part or all of an amino acid sequence described in SEQ ID NO:1, and a protein comprising a part or all of an amino acid sequence described in SEQ ID NO:1 at its N terminal. This protein may have a protease activity.

This peptide or protein consists of a part or all of an amino acid sequence present at the N terminal of the enzyme according to the present invention, or comprises a part or all of the amino acid sequence (preferably at the N terminal). Therefore, the above-mentioned peptide or protein is useful as an antigen in forming an antibody to the enzyme according to the present invention.

The present invention will be described in more detail with reference to examples, but the scope of the present invention should not be limited to these examples.

Test Procedures

The quantitative analysis of a protein was carried out by the protein staining method using Bio-Rad protein assay (Bio-Rad Co., Ltd.).

Furthermore, the detection of a protein by chromatography was carried out by measuring the absorption of an ultraviolet portion at 280 nm.

The activity of a protease was measured by the following method (a) or (b).

(a) Decomposition activity of protein with azocasein 0.05 ml of a sample enzyme solution was added to 0.3 ml of a 67 mM phosphate buffer solution (pH 7) containing 1% (W/V) azocasein, and the mixture was then kept at 30° C. for 30 minutes. Afterward, the reaction was terminated with 1 ml of a 6% trichloroacetic acid solution. After allowed to stand at room temperature for about 15 minutes, the reaction solution was centrifuged (15,000 rpm, room temperature, 10 minutes). The absorbency of the resultant supernatant liquid at 340 nm was measured by the use of a spectrophotometer. One AU was defined as the increase of 1.0 per 30 minutes in absorbance under the described conditions.

(b) Phenol Reagent Method

20 μl of a sample enzyme solution was added to 130 μl of a 100 mM glycine-sodium chloride buffer solution (pH 10) containing a 1% (W/V) substrate solution, and the mixture was kept at 30° C. for 1 hour. Afterward, the reaction was terminated by adding 150 μl of a trichloroacetic acid solution (0.11 M trichloroacetic acid, 0.22 M sodium acetate and 0.33 M acetic acid). After allowed to stand at room temperature for 30 minutes, the reaction solution was centrifuged (10,000 rpm, room temperature, 10 minutes), and 500 μl of a 0.5 M sodium carbonate solution and 100 μl of a phenol solution twice diluted with distilled water were added to 100 μl of the resultant supernatant liquid. After the solution was allowed to stand at room temperature for 1 hour, the absorbency of the solution at 660 nm was measured.

EXAMPLE 1

(Purification of protease derived from a *Flavobacterium balustinum*P104 strain)

(1) Culture of a Bacterial Strain

In order to stabilize the growth activity of bacteria, a bacterial strain was inoculated into 150 ml of the undermentioned culture medium (which was separately poured into six 100-ml Erlenmeyer flasks), and rotary shaking culture was then carried out at 10° C. for 48 hours at 140 rpm by the use of a triple shaker NR-80 (Tietec Co., Ltd.). As a main culture, 150 ml of the pre-culture medium was inoculated into 3 liters of the undermentioned culture medium, and rotary culture was then carried out at 10° C. for 75 hours at 140 rpm by the use of a laboratory fermenter LS-5 (Oriental Yeast Co., Ltd.).

| Polypeptone | 3 g/l |
| --- | --- |
| Yeast extract | 2.5 g/l |
| Sodium casein | 2.5 g/l |
| Na$_2$HPO$_4$—12H$_2$O | 3 g/l |
| MgSO$_4$—7H$_2$O | 0.2 g/l |
| (pH 7.0) | |

The culture medium and the like were sterilized with high-pressure vapor for 15 minutes under 1.2 kgf/cm$^2$ (gauge pressure) (121° C.) by an autoclave.

(2) Purification of Enzyme by the Present Invention

Every protease was purified at 4° C.

(a) Ion Exchange Chromatography

The culture medium obtained in the above-mentioned (1) was clarified by centrifugation (7,200×g, 4° C., 30 minutes). The resultant supernatant liquid was subjected to ion exchange chromatography as a crude enzyme solution. As a column, there was used an INdEX 100 column (Parmacia Biotec Co., Ltd.) filled with 2 liters of a DEAE Sephalose fast flow anion exchanger (Parmacia Biotec Co., Ltd.). A 20 mM tris buffer solution (pH 7.0) was introduced into the above-mentioned column at a linear velocity of 150 cm/hr to equilibrate the column five times or more (10 liters) as much as a gel volume.

The crude enzyme solution was introduced into the column at a linear velocity of 100 cm/hr. Elution was carried out at a linear velocity of 100 cm/hr by the use of the tris buffer solutions (pH 7.0) containing 0.2 M, 0.4 M and 0.6 M NaCl, respectively, and only portions in which a protein was detected by a UV meter were fractionated.

(b) Ultrafiltration

The fractions obtained above were treated by a new model stirring type cell 8400 (Amicon Co., Ltd.) to which a Diaflo Membrane PM30 (which can fractionate a substance having a molecular weight of 30,000 or more) (Amicon Co., Ltd.) was set, whereby proteins having a molecular weight of 30,000 or more were concentrated.

(c) Salting Out with Ammonium Sulfate

Ammonium sulfate was added to the thus concentrated solution under ice cooling so that the solution might be saturated as much as 50% with ammonium sulfate. After slow stirring at 0° C. for 4 hours, the solution was sedimented by centrifugation (27,000×g, 4° C., 20 minutes) to obtain a 0 to 50% saturated fraction. The amount of added ammonium sulfate was an amount necessary to achieve a saturated concentration at 25° C.

(d) Gel Filtration

Next, gel filtration was carried out through a HiLoad 16/60 Superdex 200 prep grade column (Parmacia Biotec Co., Ltd.). As a device, there was used HiLoad System 50 (Parmacia Biotec Co., Ltd.).

A Bis-tris buffer solution (pH 7) was caused to flow through the HiLoad 16/60 Superdex 200 prep grade column at a linear velocity of about 60 cm/hr to equilibrate the column, the amount of the Bis-tris buffer solution being three times or more (400 ml) as much as the gel volume. Afterward, 5 ml of the sample enzyme solution which had been subjected to the salting out with anmnonium sulfate was introduced into the column by the use of a Superloop. Then, elution was carried out at a linear velocity of 60 cm/hr by the use of the Bis-tris buffer solution (pH 7) as an eluent to collect fractions every 5 ml.

(e) Next, a HiLoad16/10 Q Sepharose HP column was used to carry out ion exchange chromatography. 20 mM Bis-tris buffer solution (pH 7) was introduced into the column at a linear velocity of about 150 cm/hr to equilibrate the column 5 times or more (100 ml) as much as the gel volume.

The sample enzyme solution of the protease activity fraction eluted by the gel filtration was introduced into the column at a linear velocity of 90 cm/hr by the use of the Superloop. Next, elution was carried out at a linear velocity of 90 cm/hr with 150 ml of the Bis-tris buffer solution (pH 7) containing 1M NaCl in accordance with a linear ion strength increasing gradient (0 to 1 M) to collect fractions every 5 ml.

The results of the above-mentioned purification are shown in Table 1.

TABLE 1

(Results of Purification of Protease)

|  | Amount (ml) | Protein (mg) | Enzyme Activity (AU) |
| --- | --- | --- | --- |
| Culture Medium | 1930 | 67.8 | 530 |
| DEAE Sepharose | 1850 | 43.0 | 257 |
| Ultrafiltration | 257 | 4.98 | 59.0 |
| Salting out with Ammonium Sulfate | 4 | 4.93 | 17.1 |
| Gel Filtration (Superdex 200 pg) | 16 | 0.374 | 9.53 |
| Q Sepharose | 10 | 0.299 | 6.55 |

|  | Specific Activity (×10³ AU_mg⁻¹) | Recovery Rate (%) | Purification Degree (times) |
| --- | --- | --- | --- |
| Culture Medium | 4.06 | 100 | 1 |
| DEAE Spharose | 3.22 | 48.5 | 0.794 |
| Ultrafiltration | 46.1 | 11.1 | 11.4 |
| Salting out with Ammonium Sulfate | 870 | 3 | 215 |

TABLE 1-continued (Results of Purification of Protease)

| Gel Filtration | 593 | 2 | 393 |
| --- | --- | --- | --- |
| Q Sepharose | 2192 | 1 | 540 |

EXAMPLE 3

(Measurement of purity and molecular weight of purified enzyme according to the present invention)

The purity and the molecular weight of the purified enzyme according to the present invention were measured by the use of sodium dodecylsulfate-polyacryiamide gel electrophoresis (SDS-PAGE).

A 10% polyacrylamide gel having a thickness of 1 mm was used as a support. Electrophoresis was carried out by applying 20 mA of an electric current to the gel until Bromophenol Blue (BPB) reached a lower end. The gel plate was stained with an aqueous 30% methanol-10% acetic acid solution containing 0.02% of Coomassie Brilliant Blue R250 for 1 hour, and then decolored with a decolorant (a solution of 30% of methanol and 10% of acetic acid) overnight.

Figure 1:
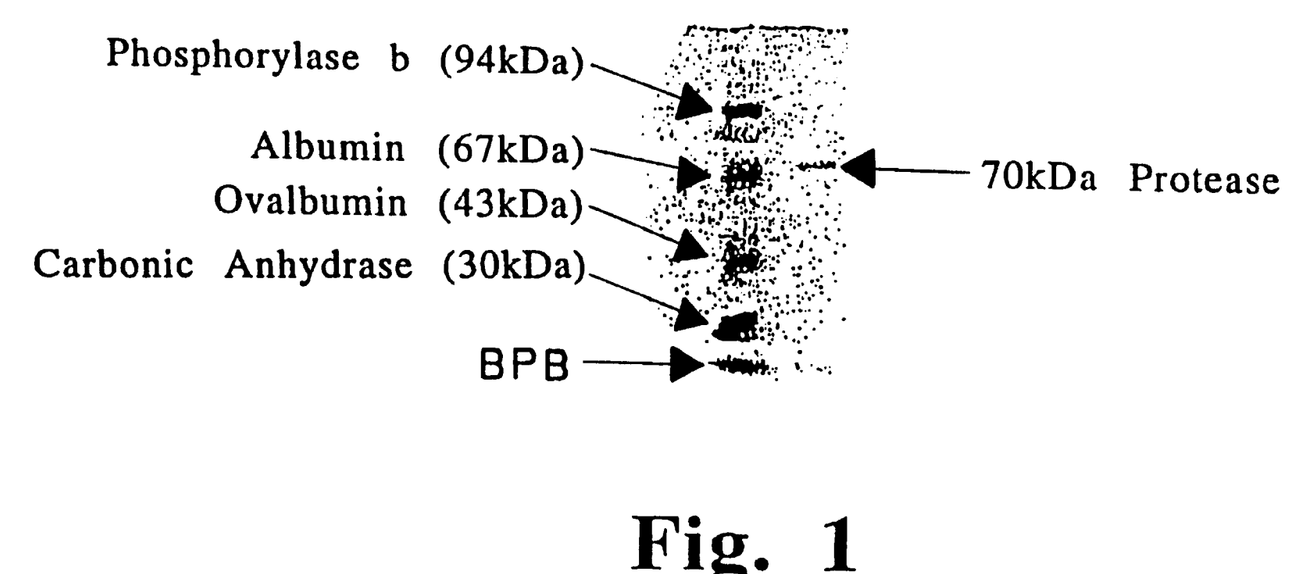
FIG. 1 is a drawing illustrating the results of the purification of an enzyme according to the present invention.
Figure 2:
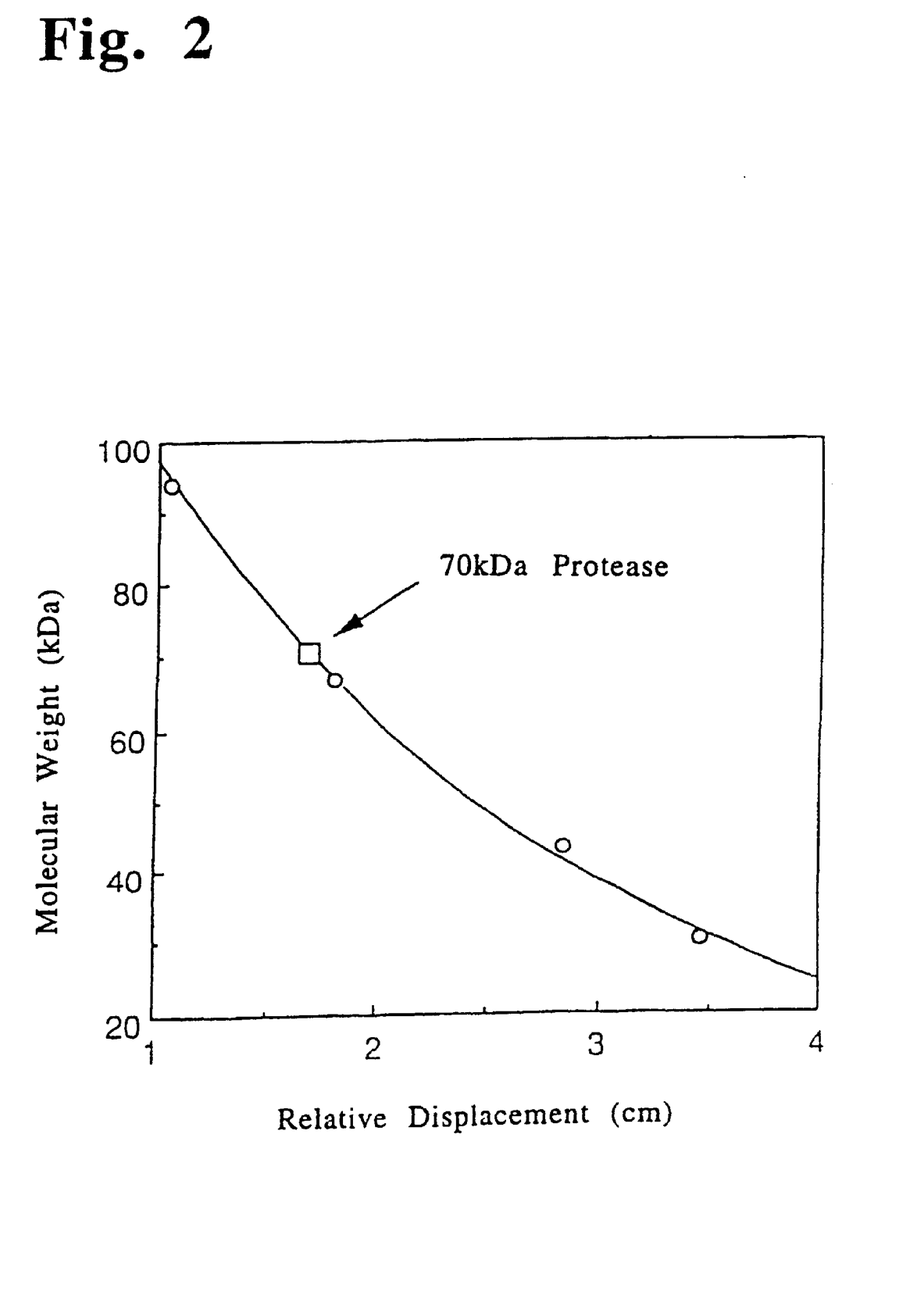
FIG. 2 is a drawing illustrating a calibration curve for measuring the molecular weight of the enzyme according to the present invention.

The results and the calibration curve of the SDS-PAGE are shown in FIGS. 1 and 2, respectively.

EXAMPLE 4

(Effect of pH on enzyme reaction)

Azocasein was decomposed with the enzyme of the present invention at various pH values. Buffer solutions for a reaction solution had each a concentration of 100 mM and they were a sodium acetate-acetic acid buffer solution (pH 4.0–5.5), MES (2-morpholinoethanesulfonic acid monohydrate) buffer solution (pH 5.5–6.5), MOPS (3-morpholinopropanesulfonic acid) buffer solution (pH 6.5–8.0), TAPS (N-tris(hydroxymethyl)methyl-3-aminopropanesulfonic acid) buffer solution (pH 8.0–9.0), CHES (N-cyclohexyl-2-aminoethanesulfonic acid) buffer solution (pH 9.0–10.0), CAPS (N-cyclohexyl-3-aminopropanesulfonic acid) buffer solution (pH 10.0–11.0) and glycine-sodium chloride-sodium hydroxide buffer solution (pH 11.0–13.0).

Figure 3:
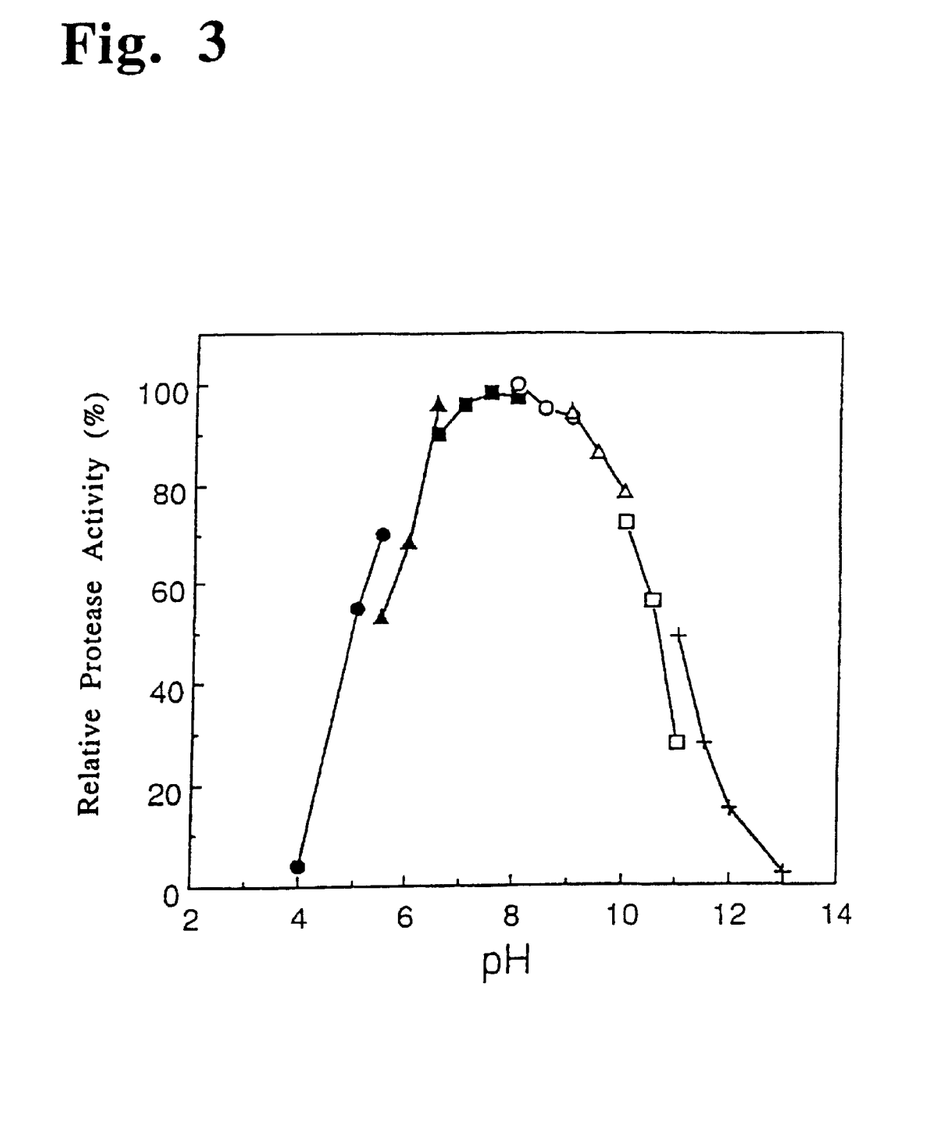
FIG. 3 is a drawing illustrating the effect of pH on an enzyme reaction of the enzyme according to the present invention. Each black circle represents the enzyme according to the present invention at pH 7, each black triangle represents the enzyme according to the present invention at pH 10, and each white square represents Savinase at pH7.

The results are shown in FIG. 3.

The relative activity of the enzyme at pH 8.0 which was an optimal pH was maintained as much as about 90% or more in the range of pH 6.5 to pH 9.5. Thus, it is apparent that the enzyme of the present invention acts in a considerably wide range where a neutral pH is a center. However, the enzyme did not act sufficiently in an acidic pH range of pH 5.0 or less and an alkaine pH range of pH 11.0 or more, and the protease was inactivated at pH 13.0.

EXAMPLE 5

(pH stability of enzyme according to the present invention)

Figure 4:
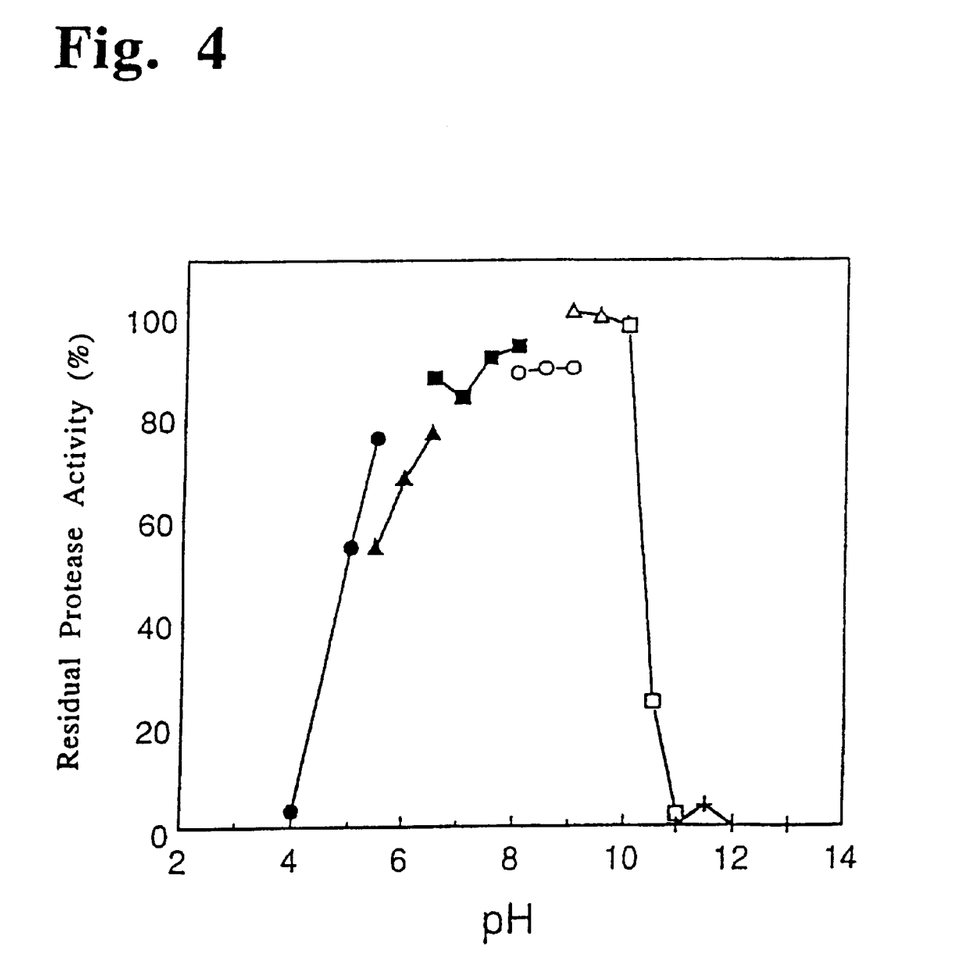
FIG. 4 is a drawing illustrating the pH stability of the enzyme according to the present invention. Each black circle represents a measured value at 10° C., each black triangle represents a measured value at 20° C., each black square represents a measured value at 30° C., each white circle represents a measured value at 40° C., each white triangle represents a measured value at 50° C., and each white square represents a measured value at 60° C.

The enzyme according to the present invention was maintained in each of the above-mentioned buffer solutions at 30° C. for 1 hour, and the remaining protease activity was then inspected. The results are shown in FIG. 4.

It was found that the enzyme according to the present invention was stable over the range of pH 6.5 to pH 10.0 at 30° C. for 1 hour, but the same was inactivated at pH 4.0 and pH 11.0 under the same conditions.

EXAMPLE 6

(Effect of temperature on enzyme reaction)

Figure 5:
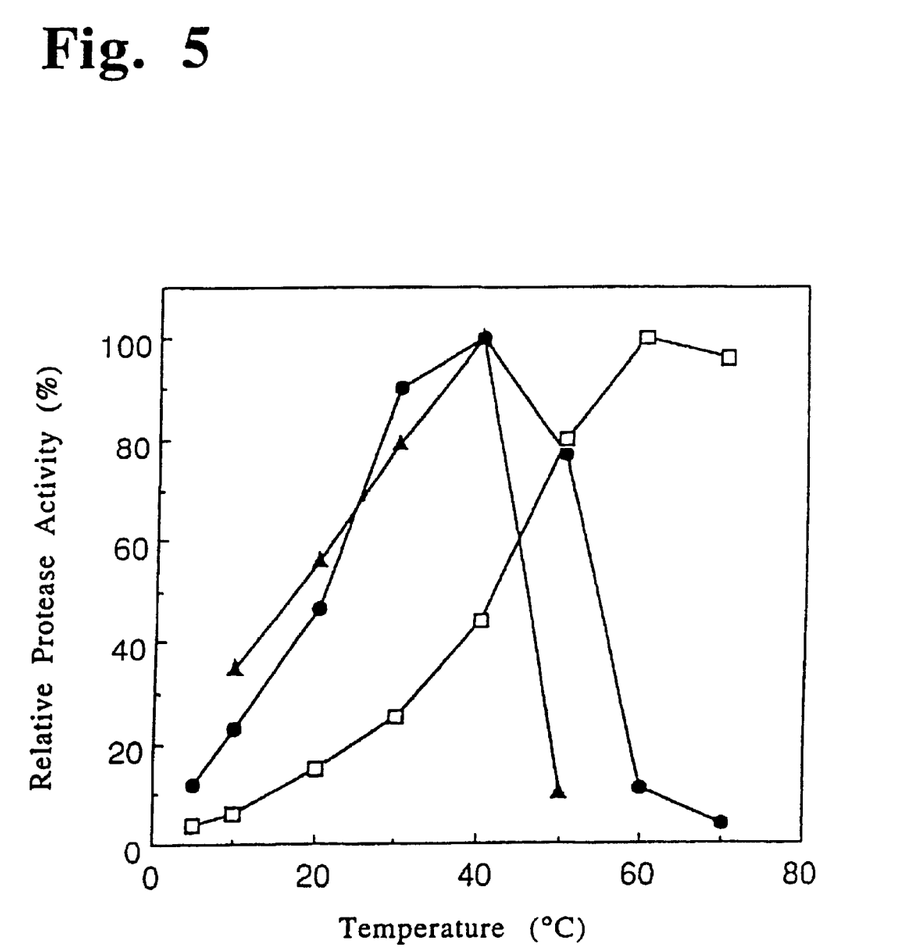
FIG. 5 is a drawing illustrating the effect of temperature on the enzyme reaction of the enzyme according to the present invention.

Azocasein was decomposed with the enzyme according to the present invention at various temperatures in a 67 mM phosphoric acid buffer solution (pH 7) and a 100 mM glycine-sodium chloride (pH 10). The reaction temperatures were changed from 5° C. to 70° C. Furthermore, also with regard to a commercially available enzyme, Savinase (Novonordisc Co., Ltd.), an influence of a temperature at pH 7 was measured. The results are shown in FIG. 5.

The optimal temperature of the enzyme according to the present invention at pH 10 and pH 7 were 40° C. At a temperature of 30° C., the enzyme of the present invention could maintain about 80% of the activity at pH 10 and about 90% of the activity at pH 7. At a temperature of 50° C., the enzyme of the present invention could maintain about 10% of the activity at pH 10 and about 80% of the activity at pH 7. The optimal temperature of commercially available Savinase was 60° C., which was much higher as compared with that of the enzyme according to the present invention.

EXAMPLE 7

(Temperature stability of enzyme according to the present invention)

Figure 6:
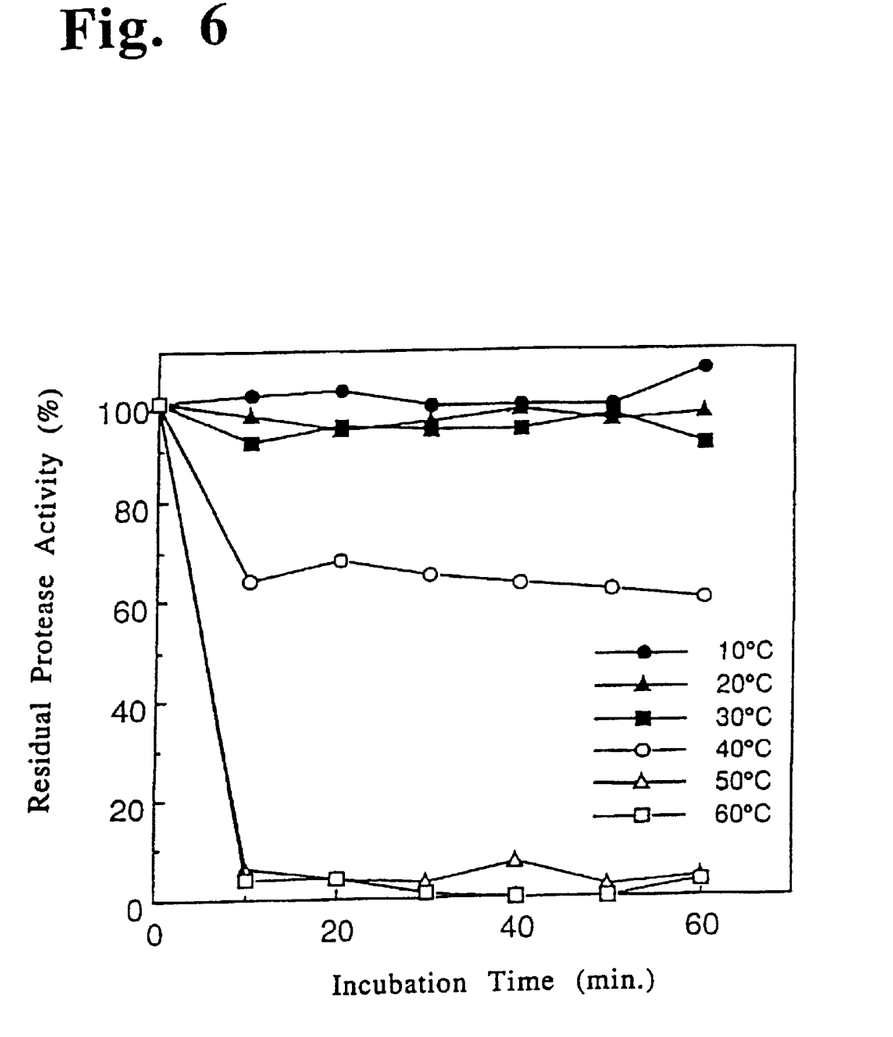
FIG. 6 is a drawing illustrating the temperature stability of the enzyme according to the present invention.

The enzyme according to the present invention was maintained at 10 to 60° C. for hour. The variation of its activity with time is shown in FIG. 6.

The enzyme according to the present invention was scarcely inactivated at 10° C., 20° C. and 30° C. for 1 hour. However, it was inactivated at 40° C. to about 60% of the protease activity, and afterward, it was gradually inactivated. At 50° C. and 60° C., the enzyme was rapidly inactivated, and it was completely inactivated in 10 minutes.

EXAMPLE 8

(Effect of inhibitor on enzyme according to the present invention)

As inhibitors, there were used pepstatin acting on aspartic protease, L-trans-epoxysuccinylleucylamido-4-guanidinobutane (E-64) and iodoacetamide acting on cysteine protease, phenylmethanesulfonyl fluoride (PMSF) acting on serine protease, 1,10-phenanthroline and ethylenediaminetetraacetic acid (EDTA) acting on metal protease and metal-dependent protease. These inhibitors were added to an enzyme reaction system so as to become various final concentrations, and the reaction system was then maintained at 30° C. for 0.5 or 1 hour to inspect the remaining protease activity. The results are shown in Table 2.

The protease activity of the enzyme according to the present invention was not inhibited by pepstatin, L-trans-epoxysuccinylleucylamido-4-guanidinobutane (E-64), iodoacetamide and 1,10-phenanthroline, but it was notably inhibited by phenylmethanesulfonyl fluoride (PMSF) and ethylenediamnietetraacetic acid (EDTA). From these results, it is implied that the enzyme according to the present invention is serine protease in which an active center is serine.

EXAMPLE 9

(Substrate specificity of protease)

The proteolytic activities of the protease to casein, hemoglobin, albumin and gelatin as substrate proteins were measured by a phenol reagent method. The results are shown in Table 3.

TABLE 3

(Substrate Specificity)

| Substrate | Specific Enzyme Activity |
| --- | --- |
| Casein | 100 |
| Glatin | 51 |
| Hemoglobin | 30 |
| Albumin | 13 |

The enzyme according to the present invention specifically acted on casein at a low temperature, and the substrate specificity of the enzyme decreased in the order of gelatin, hemoglobin and albumin.

EXAMPLE 10

(Determination of amino acid sequence at N terminal)

In the enzyme according to the present invention, 30 residues of the amino acid sequence at its N terminal were determined. The results are shown in SEQ ID NO:1.

The amino acid sequence at the N terminal of the enzyme according to the present invention was determined, and its homology with known amino acid sequences was inspected by the use of a data bank "Entrez". As a result, it was apparent that there was no homology. Accordingly, since the enzyme according to the present invention has no homology with any amino acid sequences of known proteins, it has been confirmed that the enzyme according to the present invention possesses the novel amino acid sequence at the N terminal.

What is claimed is:

1. An isolated protein from *Flavobacterium balustinum* consisting of an amino acid sequence of SEQ ID NO:1.

* * * * *

SEQUENCE LISTING

```
<160> NUMBER OF SEQ ID NOS: 1

<210> SEQ ID NO 1
<211> LENGTH: 30
<212> TYPE: PRT
<213> ORGANISM: Flavobacterium balustinum

<400> SEQUENCE: 1
```

-continued

```
Asp Thr Arg Gln Leu Leu Asn Ala Asn Ser Asp Leu Leu Asn Thr Thr
 1               5                  10                  15

Gly Asn Val Thr Gly Leu Thr Gly Ala Phe Asn Gly Glu Asn
            20                  25                  30
```